United States Patent
Wang et al.

(10) Patent No.: US 9,634,266 B2
(45) Date of Patent: Apr. 25, 2017

(54) ORGANIC METAL COMPOUND, ORGANIC LIGHT-EMITTING DEVICE, AND LIGHTING DEVICE EMPLOYING THE SAME

(71) Applicant: INDUSTRIAL TECHNOLOGY RESEARCH INSTITUTE, Hsinchu (TW)

(72) Inventors: Yi-Rong Wang, Taipei (TW); Chih-Lung Chin, Hsinchu (TW); Wan-Chi Chen, Sinwu Township (TW); Shih-Hsien Liu, Jhubei (TW); Kung-Lung Cheng, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 189 days.

(21) Appl. No.: 14/576,483

(22) Filed: Dec. 19, 2014

(65) Prior Publication Data

US 2015/0179960 A1    Jun. 25, 2015

(30) Foreign Application Priority Data

Dec. 25, 2013  (TW) .............. 102148203 A

(51) Int. Cl.
  *H01L 51/00*  (2006.01)
  *C07F 15/00*  (2006.01)
  *H01L 51/50*  (2006.01)

(52) U.S. Cl.
  CPC ...... *H01L 51/0085* (2013.01); *C07F 15/0033* (2013.01); *H01L 51/5016* (2013.01)

(58) Field of Classification Search
  CPC ............. H01L 51/0085; H01L 51/5016; C07F 15/0033
  See application file for complete search history.

(56) References Cited

U.S. PATENT DOCUMENTS

| | | | |
|---|---|---|---|
| 7,445,857 B2 | 11/2008 | Shen et al. | |
| 7,799,918 B2 * | 9/2010 | Chin | C07D 213/72 428/690 |
| 8,142,909 B2 | 3/2012 | Beers et al. | |
| 8,471,248 B2 | 6/2013 | Schmidhalter et al. | |
| 2001/0015432 A1 | 8/2001 | Igarashi | |
| 2006/0054904 A1 * | 3/2006 | Lin | H01L 25/0753 257/88 |
| 2008/0214818 A1 * | 9/2008 | Chin | C07D 213/72 546/81 |
| 2008/0297033 A1 | 12/2008 | Knowles et al. | |
| 2012/0199794 A1 | 8/2012 | Stoessel et al. | |

FOREIGN PATENT DOCUMENTS

| | | |
|---|---|---|
| TW | 200827369 | 7/2008 |
| WO | WO 02/074015 A2 | 9/2002 |

OTHER PUBLICATIONS

Jou et al, Highly Efficient Yellow Organic Light Emitting Diode with a Novel Wet- and Dry-Process Feasible Iridium Complex Emitter, Advanced Functional Materials, vol. 24, pp. 555-562, Aug. 5, 2013.*
Baldo et al., "Very high efficiency green organic light-emitting devices based on electrophosphorescence", Applied Physics Letters, Jul. 5, 1999, vol. 75, No. 1, pp. 3-6.
Di Censo et al., "Synthesis, Characterization, and DFT/TD-DFT Calculations of Highly Phosphorescent Blue Light-Emitting Anionic Iridium Complexes", Inorganic Chemistry, 2008, vol. 47, No. 3, pp. 980-989.
Hsieh et al., "Design and Synthesis of Iridium Bis(carbene) Complexes for Efficient Blue Electrophosphorescence", Chem. Eur. J., 2011, vol. 17, pp. 9180-9187.
Kozhevnikov et al., "Cyclometalated Ir(III) Complexes for High-Efficiency Solution-Processable Blue PhOLEDs", American Chemical Society, Apr. 3, 2013, A-G.
Yun et al., "Sky-blue phosphorescent iridium(III) complexes with two substituted 2-phenylpyridine derivatives and one picolinic acid for organic light-emitting diodes", Elsevier, Journal of Organometallic Chemistry, 2013, vol. 724, pp. 244-250.
Chinese Office Action and Search Report dated Nov. 28, 2016, for Chinese Application No. 201310743838.5.
Jou et al., "Highly efficient green organic light emitting diode with a novel solution processable iridium complex emitter," J. Mater. Chem. C, 2013, vol. 1, pp. 4201-4208.

* cited by examiner

*Primary Examiner* — Alexander Kollias
(74) *Attorney, Agent, or Firm* — Birch, Stewart, Kolasch & Birch, LLP

(57) ABSTRACT

Organic metal compounds, organic light-emitting devices, and lighting devices employing the same are provided. The organic metal compound has a chemical structure represented by Formula (I):

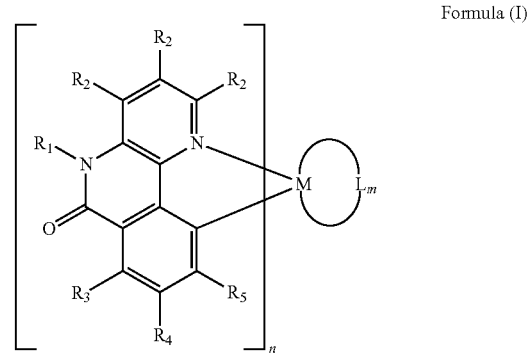

Formula (I)

wherein M is Ir, Pt, Ru, Os, Cu, Au, or Pd; n is 1, 2, or 3; m is 0, 1, or 2, and the sum of m and n is equal to a valence of M; L is a bidentate ligand; $R_1$ is hydrogen, $C_{1-9}$ alkyl group, $C_{5-10}$ cycloalkyl group, or $C_{5-12}$ aromatic group; each of $R_2$ is independent and can be hydrogen, halogen, cyano group, $C_{1-9}$ alkyl group, $C_{1-6}$ fluoroalkyl group, $C_{5-10}$ cycloalkyl group, or $C_{5-12}$ aromatic group; $R_3$ is halogen; and, $R_4$ and $R_5$ are independently the same or different hydrogen, hydroxyl group, amine group, alkyl amine group, halogen, cyano group, $C_{1-9}$ alkyl group, $C_{1-6}$ fluoroalkyl group, $C_{5-10}$ cycloalkyl group, or $C_{5-12}$ aromatic group.

21 Claims, 3 Drawing Sheets

ORGANIC METAL COMPOUND, ORGANIC LIGHT-EMITTING DEVICE, AND LIGHTING DEVICE EMPLOYING THE SAME

CROSS REFERENCE TO RELATED APPLICATIONS

This application is based upon and claims the benefit of priority from the prior Taiwan Patent Application No. 102148203, filed on 25 Dec. 2013, the entire contents of which are incorporated herein by reference.

TECHNICAL FIELD

The disclosure relates to an organic metal compound, an organic light-emitting device, and a lighting device employing the same.

BACKGROUND

An organic light-emitting diode (OLED) is a light-emitting diode employing an organic light-emitting layer as an active layer. OLED display devices have high luminescent efficiency and long operating lifespans. In comparison with liquid-crystal displays, due to the characteristics of spontaneous emission, a device employing an organic light-emitting diode is free of a back-light source.

Generally, an organic electroluminescent device is composed of a light-light-emitting layer sandwiched between a pair of electrodes. When an electric field is applied to the electrodes, the cathode injects electrons into the light-emitting layer and the anode injects holes into the light-emitting layer. When the electrons recombine with the holes in the light-emitting layer, excitons are formed. Recombination of the electron and hole results in light emission.

Depending on the spin states of the hole and electron, the exciton can have either a triplet or singlet spin state. Luminescence from a singlet exciton results in fluorescence whereas luminescence from a triplet exciton results in phosphorescence. The luminescent efficiency of phosphorescence is three times that of fluorescence.

Therefore, it is crucial to develop highly efficient phosphorescent material in order to increase the luminescent efficiency of an OLED.

SUMMARY

According to an embodiment of the disclosure, the disclosure provides an organic metal compound having Formula (I):

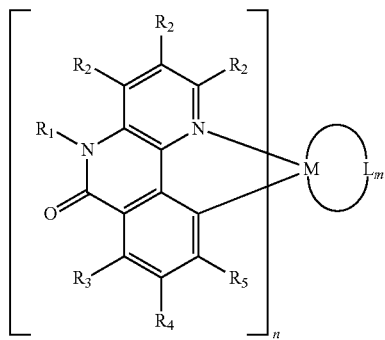

Formula (I)

wherein, M is Ir, Pt, Ru, Os, Cu, Au, or Pd; n is 1, 2, or 3, m is 0, 1, or 2, and the sum of m and n is equal to the valence of M; L is a bidentate ligand; $R_1$ is hydrogen, $C_{1-9}$ alkyl group, $C_{5-10}$ cycloalkyl group, or $C_{5-12}$ aromatic group; each of $R_2$ is independent and can be hydrogen, halogen, cyano group, $C_{1-9}$ alkyl group, $C_{1-6}$ fluoroalkyl group, $C_{5-10}$ cycloalkyl group, or $C_{5-12}$ aromatic group; $R_3$ is halogen; and $R_4$ and $R_5$ are independently hydrogen, hydroxyl group, amine group, alkyl amine group, halogen, cyano group, $C_{1-9}$ alkyl group, $C_{1-6}$ fluoroalkyl group, $C_{5-10}$ cycloalkyl group, or $C_{5-12}$ aromatic group.

According to another embodiment of the disclosure, the disclosure also provides an organic light-emitting device, which includes a pair of electrodes; and an organic light-emitting element disposed between the electrodes, wherein the organic light-emitting element includes the aforementioned organic metal compound.

According to other embodiments of the disclosure, the disclosure also provides a lighting device including: a lead frame; and the aforementioned organic light-emitting device disposed on the lead frame.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION

Figure 1:
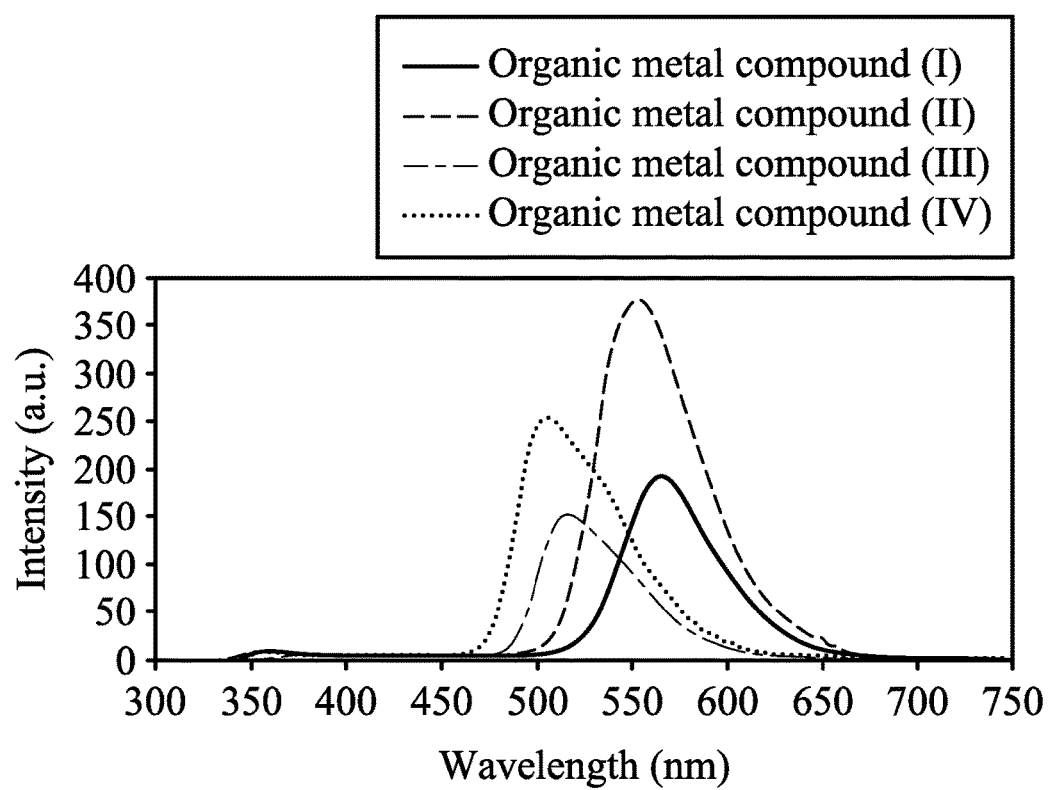
FIG. 1 shows photoluminescence excitation spectra of the organic metal compounds (I)-(IV) of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Organic Metal Compound

According to embodiments of the disclosure, the disclosure provides an organic metal compound having Formula (I):

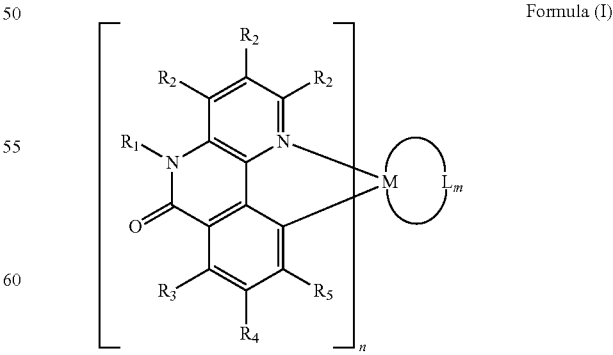

Formula (I)

wherein, M is Ir, Pt, Ru, Os, Cu, Au, or Pd; n is 1, 2, or 3, m is 0, 1, or 2, and a sum of m and n is equal to a valence of M; L is a bidentate ligand; $R_1$ is hydrogen, $C_{1-9}$ alkyl group, $C_{5-10}$ cycloalkyl group, or $C_{5-12}$ aromatic group; each of $R_2$ is independent and can be hydrogen, halogen, cyano group, $C_{1-9}$ alkyl group, $C_{1-6}$ fluoroalkyl group, $C_{5-10}$ cycloalkyl group, or $C_{5-12}$ aromatic group; $R_3$ is halogen; and, $R_4$ and $R_5$ are independently hydrogen, hydroxyl group, amine group, alkyl amine group, halogen, cyano group, $C_{1-9}$ alkyl group, $C_{1-6}$ fluoroalkyl group, $C_{5-10}$ cycloalkyl group, or $C_{5-12}$ aromatic group.

The organic metal compounds of the disclosure can serve as a phosphorescent dopant material (having a maximum luminous intensity peak of between about 540 nm to 570 nm), and can be applied to an organic light-emitting device for enhancing the luminescent efficiency.

According to embodiments of the disclosure, $R_1$ can be hydrogen, methyl group, ethyl group, propyl group, isopropyl group, butyl group, iso-butyl group, tert-butyl group, pentyl group, hexyl group, cyclohexyl group, phenyl group, biphenyl group, or naphthyl group. Further, each of $R_2$ can be independently hydrogen, fluorine, chlorine, cyano group, methyl group, ethyl group, propyl group, isopropyl group, butyl group, iso-butyl group, tert-butyl group, pentyl group, hexyl group, fluoromethyl (such as monofluoromethyl, difluoromethyl, or trifluoromethyl), fluoroethyl, cyclohexyl group, phenyl group, biphenyl group, or naphthyl group. Moreover, $R_3$ can be fluorine, or chlorine; and, $R_4$ and $R_5$ are independently hydrogen, hydroxyl group, fluorine, chlorine, cyano group, amine group, dimethyl amine group, diethyl amine group, methyl group, ethyl group, propyl group, isopropyl group, butyl group, iso-butyl group, tert-butyl group, pentyl group, hexyl group, fluoromethyl group (such as monofluoromethyl, difluoromethyl, or trifluoromethyl), fluoroethyl group, cyclohexyl group, phenyl group, biphenyl group, or naphthyl group.

According to some embodiments of the disclosure, at least one of $R_2$ of the organic metal compound having Formula (I) is not hydrogen. Further, $R_3$, $R_4$, and $R_5$ can be the same or different.

According to other embodiments of the disclosure, the central metal atom M of the organic metal compound can be bonded with two atoms of the bidentate ligand L, wherein L is bonded with M via an oxygen atom on one side, and bonded with M via another oxygen atom on the other side. For example, L can be

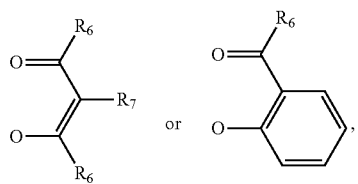

wherein each of $R_6$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group, and $R_7$ is hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group.

According to other embodiments of the disclosure, L is bonded with M via a nitrogen atom on one side, and bonded with M via another nitrogen atom on the other side. For example, L can be

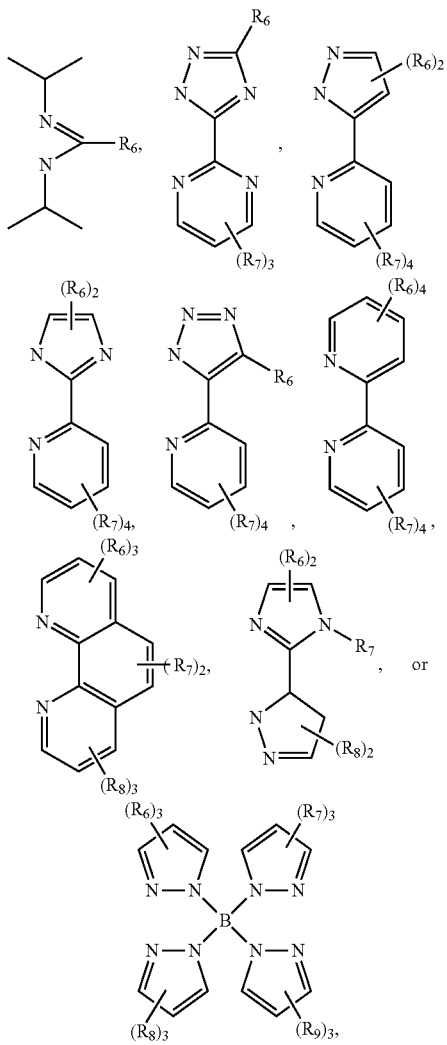

wherein each of $R_6$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; each of $R_7$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; each of $R_8$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; and, each of $R_9$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group.

According to other embodiments of the disclosure, L is bonded with M via a nitrogen atom on one side, and bonded with M via an oxygen atom on the other side. For example, L can be

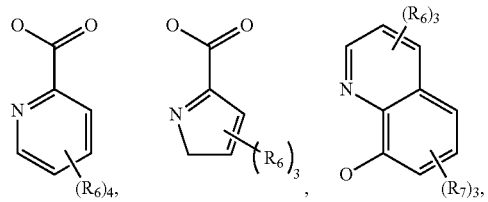

-continued

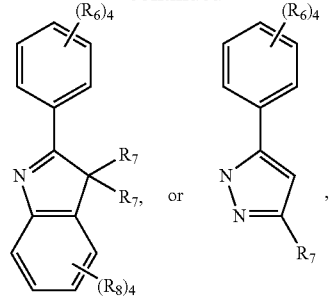

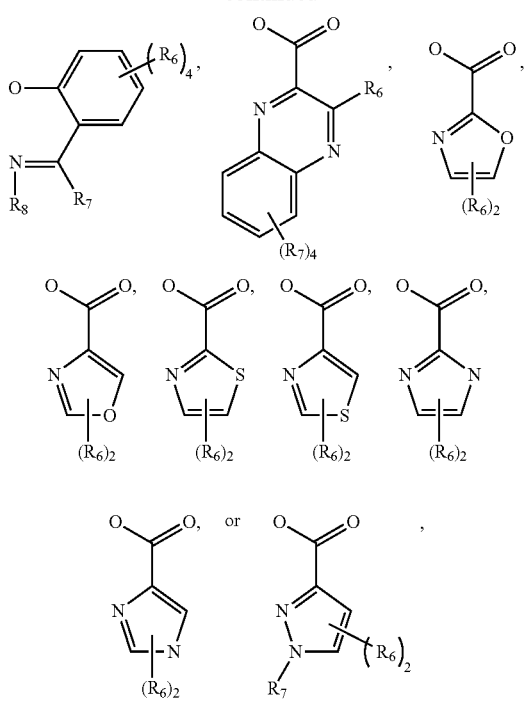

wherein each of $R_6$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; and, each of $R_7$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group.

According to other embodiments of the disclosure, L is bonded with M via a nitrogen atom on one side, and bonded with M via a carbon atom on the other side. For example, L can be

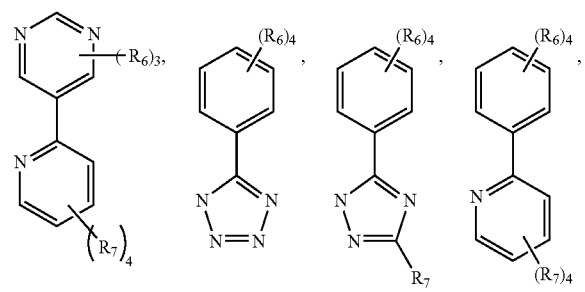

wherein each of $R_6$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; each of $R_7$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; and, each of $R_8$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group.

According to embodiments of the disclosure, the organic metal compound can be

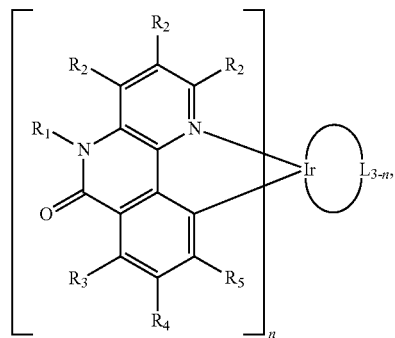

wherein n is 1, or 2; L is a bidentate ligand; $R_1$ is hydrogen, $C_{1-9}$ alkyl group, $C_{5-10}$ cycloalkyl group, or $C_{5-12}$ aromatic group; each of $R_2$ is independent and can be hydrogen, halogen, cyano group, $C_{1-9}$ alkyl group, $C_{1-6}$ fluoroalkyl group, $C_{5-10}$ cycloalkyl group, or $C_{5-12}$ aromatic group; $R_3$ is halogen; and, $R_4$ and $R_5$ are independently hydrogen, hydroxyl group, amine group, alkyl amine group, halogen, cyano group, $C_{1-9}$ alkyl group, $C_{1-6}$ fluoroalkyl group, $C_{5-10}$ cycloalkyl group, or $C_{5-12}$ aromatic group.

According to embodiments of the disclosure, the organic metal compound can be

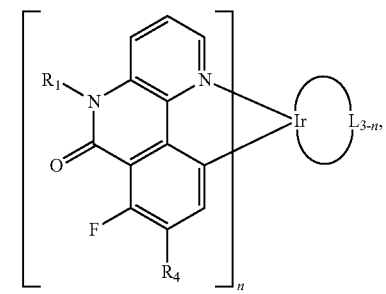

wherein, n is 1, or 2; L is a bidentate ligand; $R_1$ is hydrogen, $C_{1-9}$ alkyl group, $C_{5-10}$ cycloalkyl group, or $C_{5-12}$ aromatic group; and, $R_4$ is hydrogen, hydroxyl group, amine group, alkyl amine group, halogen, cyano group, $C_{1-9}$ alkyl group, $C_{1-6}$ fluoroalkyl group, $C_{5-10}$ cycloalkyl group, or $C_{5-12}$ aromatic group.

According to embodiments of the disclosure, the organic metal compound can be

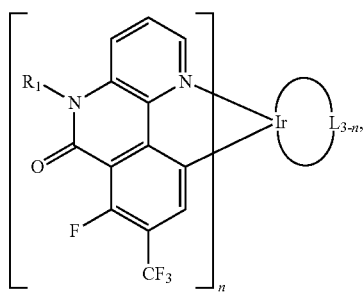

wherein, n is 1, or 2; L is a bidentate ligand; $R_1$ is hydrogen, $C_{1-9}$ alkyl group, $C_{o5-1}$ cycloalkyl group, or $C_{5-12}$ aromatic group.

On the other hand, in order to enhance the luminescent efficiency within the wavelength range of 540-570 nm of the organic light-emitting device employing the organic metal compound, the organic metal compound can be

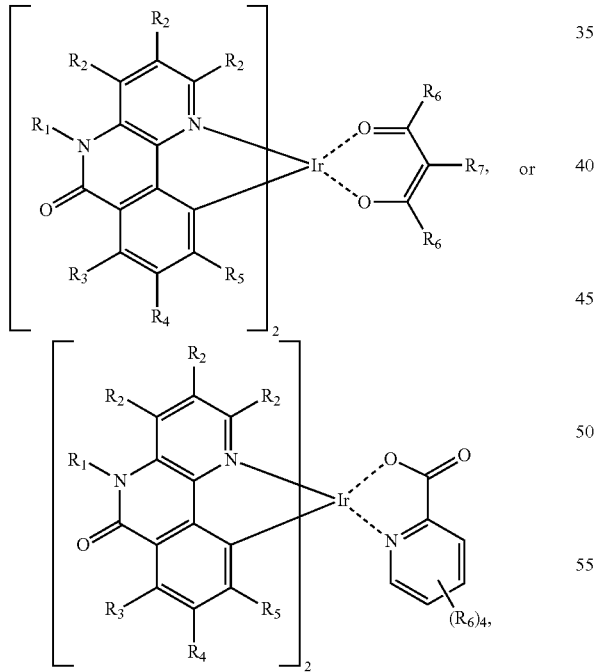

wherein, $R_1$ is hydrogen, $C_{1-9}$ alkyl group, $C_{5-10}$ cycloalkyl group, or $C_{5-12}$ aromatic group; each of $R_2$ is independent and can be hydrogen, halogen, cyano group, $C_{1-9}$ alkyl group, $C_{1-6}$ fluoroalkyl group, $C_{5-19}$ cycloalkyl group, or $C_{5-12}$ aromatic group; $R_3$ is halogen; and, $R_4$ and $R_5$ are independently hydrogen, hydroxyl group, amine group, alkyl amine group, halogen, cyano group, $C_{1-9}$ alkyl group, $C_{1-6}$ fluoroalkyl group, $C_{5-10}$ cycloalkyl group, or $C_{5-12}$ aromatic group; each of $R_6$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; and, $R_7$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group. For example, each of $R_2$ is hydrogen, $R_3$ is halogen, $R_4$ is C1-6 fluoroalkyl group, $R_5$ is hydrogen, and $R_6$ and $R_7$ are as defined above.

According to embodiments of the disclosure, the organic metal compound having Formula (I) of the disclosure can be

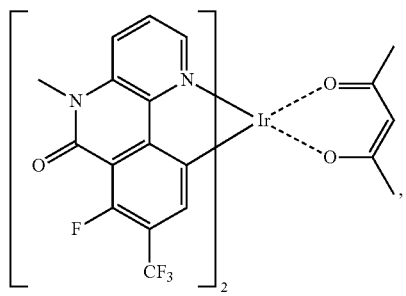

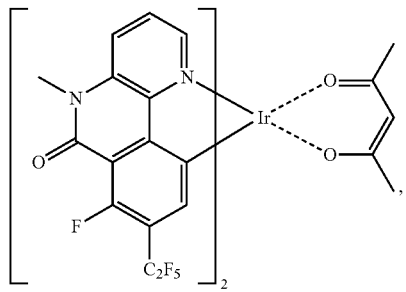

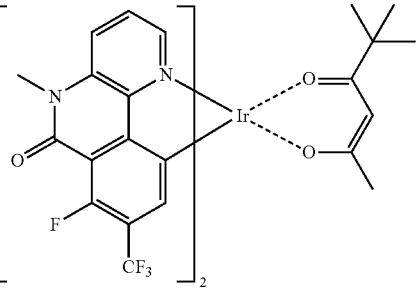

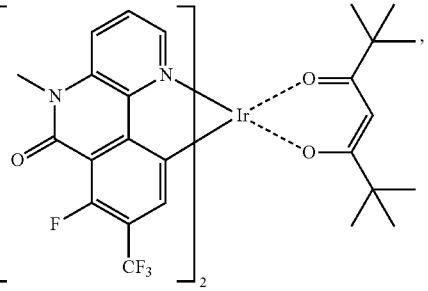

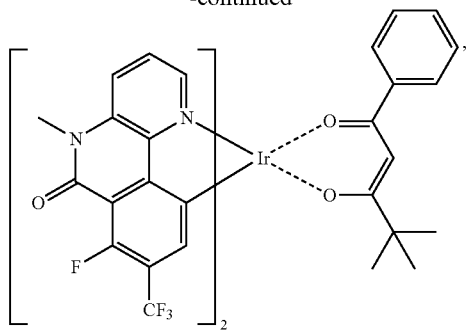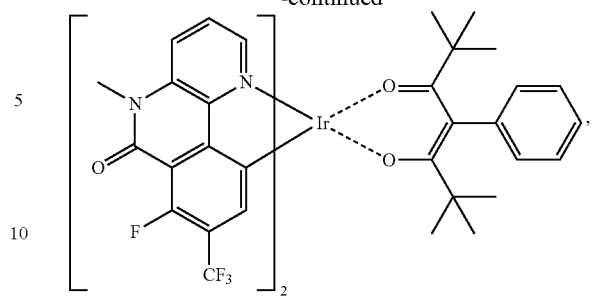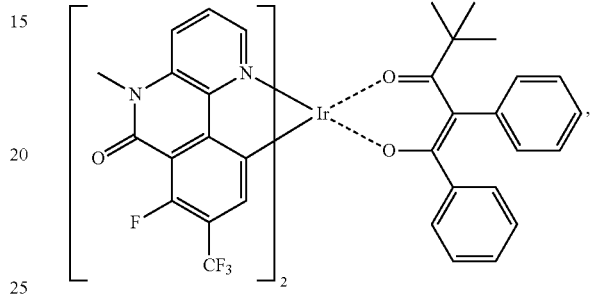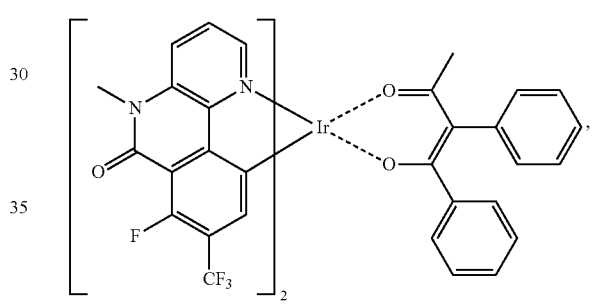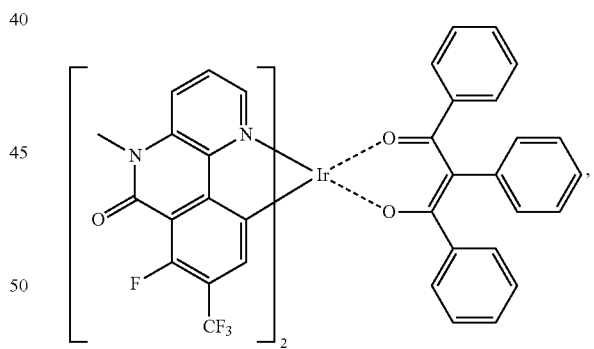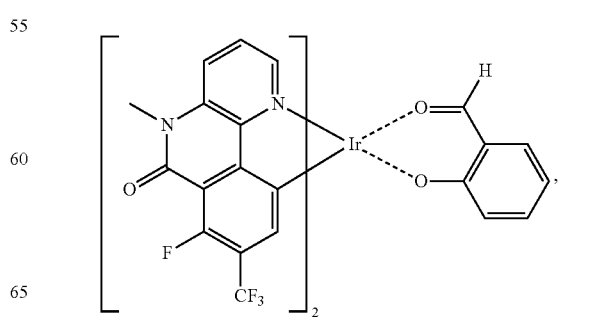

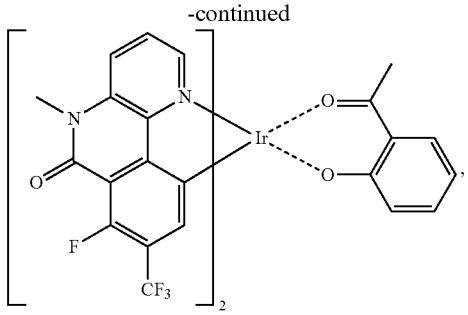
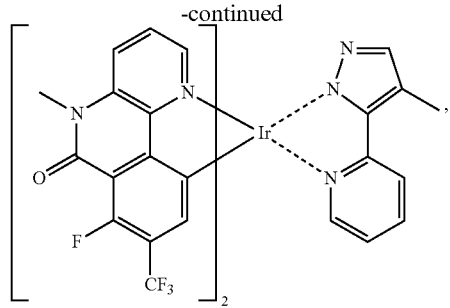
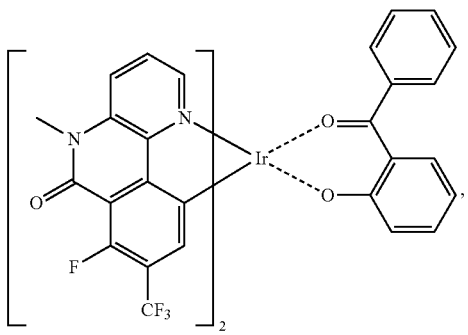
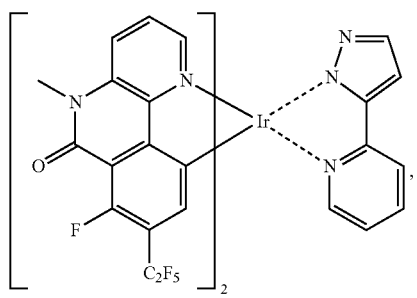
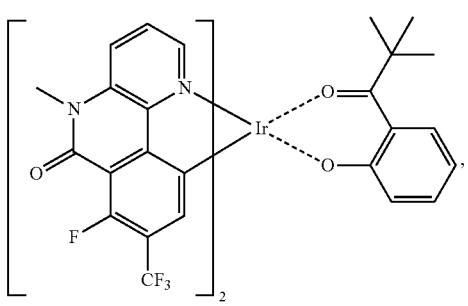
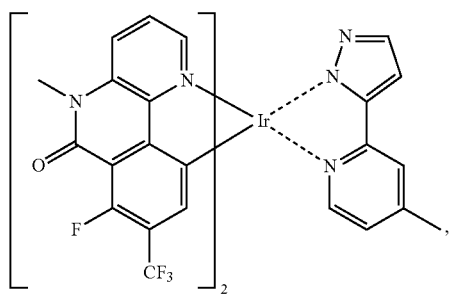
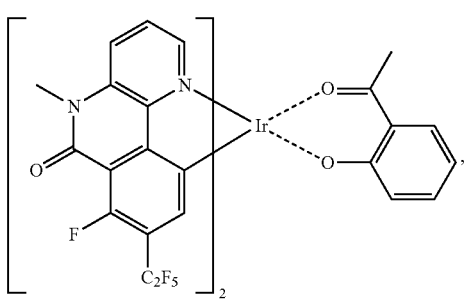
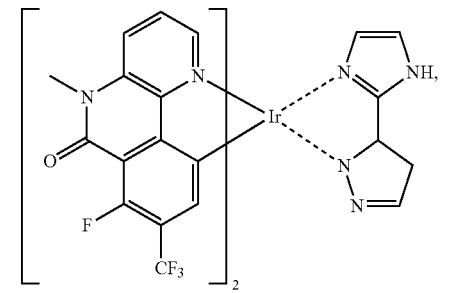
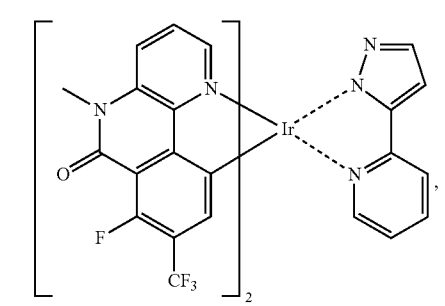
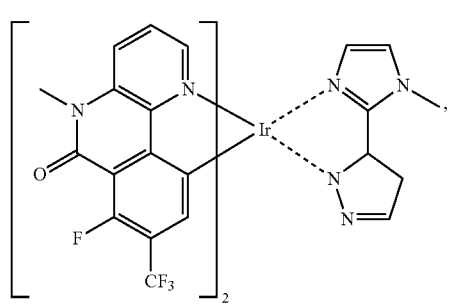

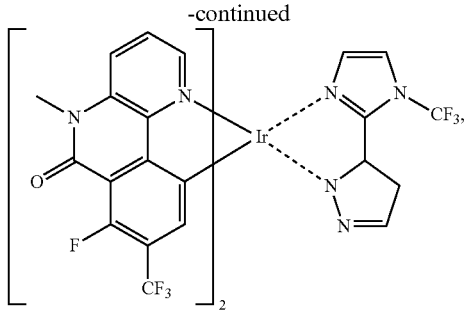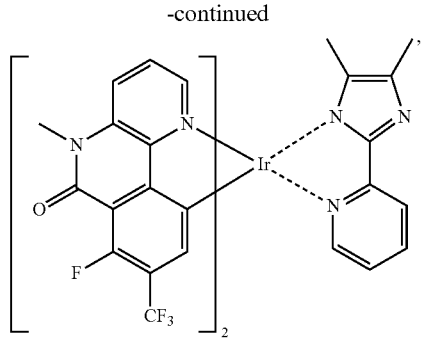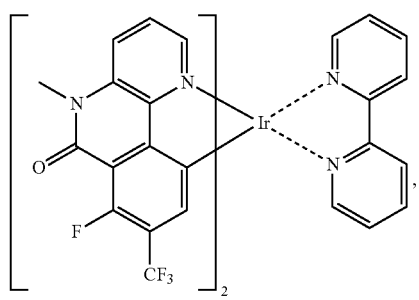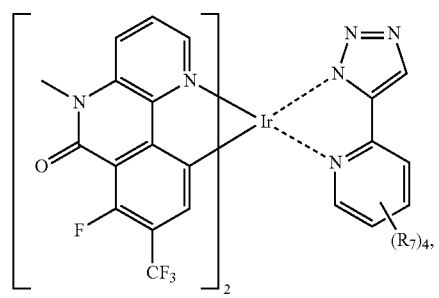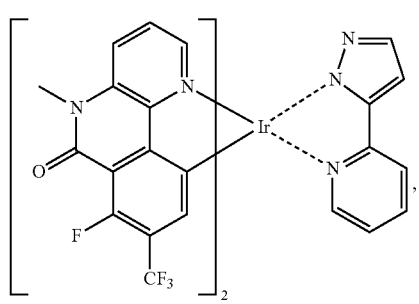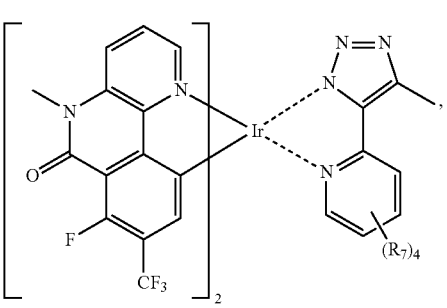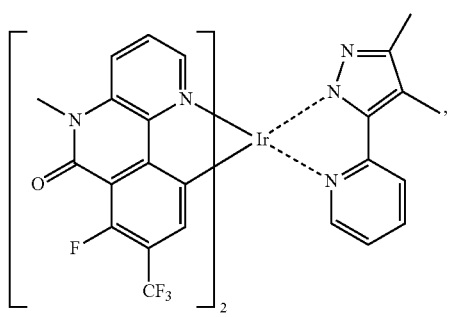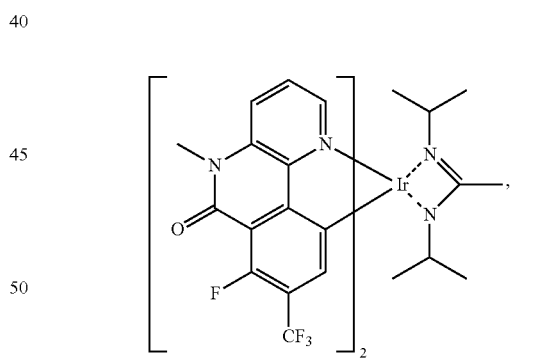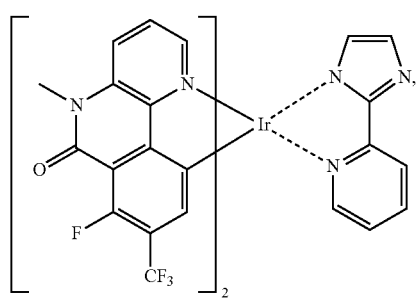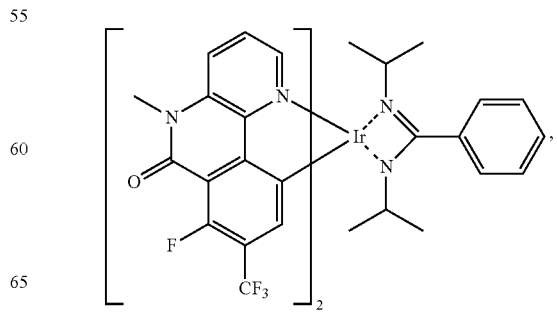

-continued
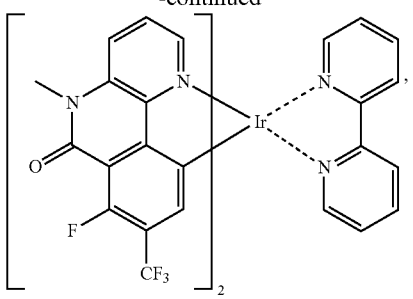
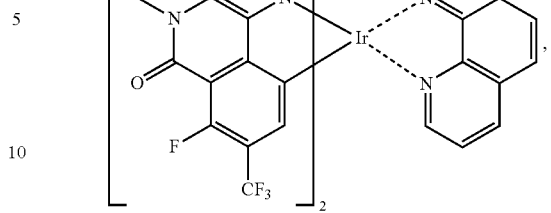
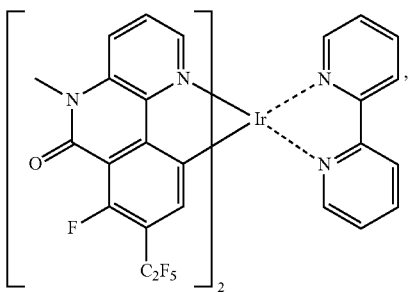
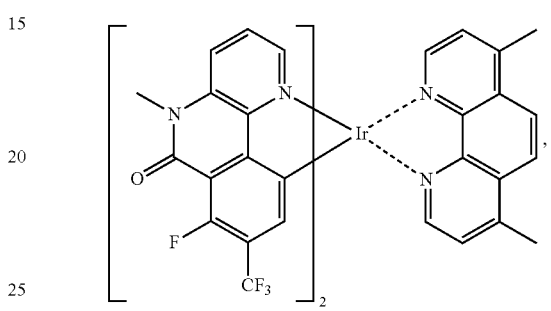
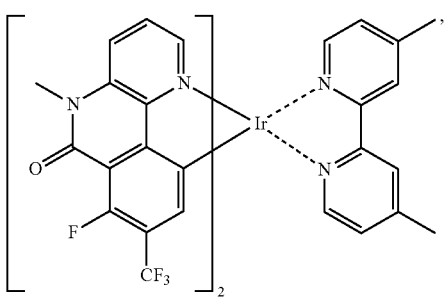
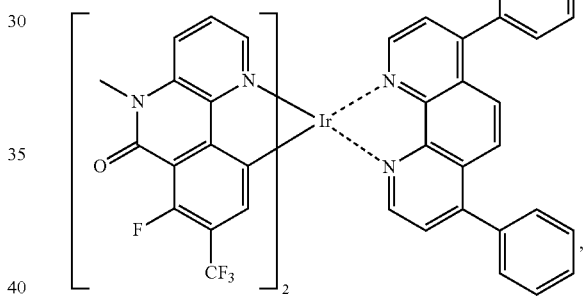
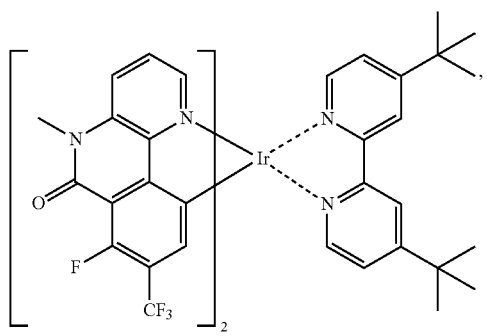
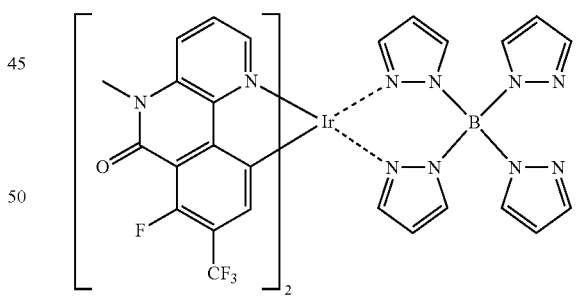
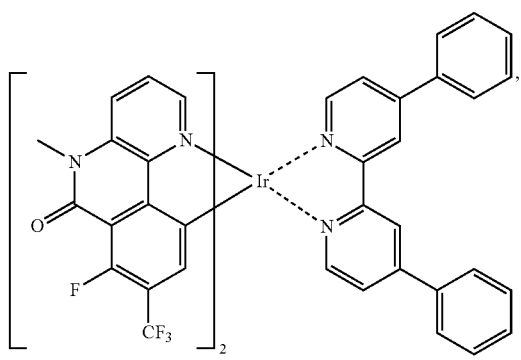
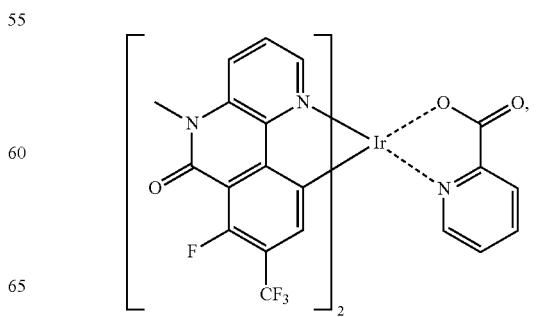

-continued
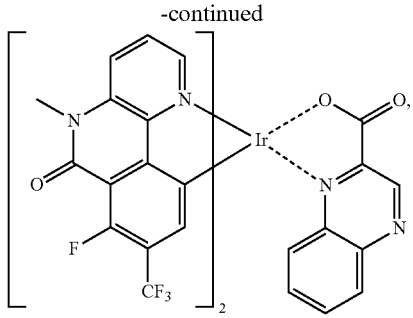
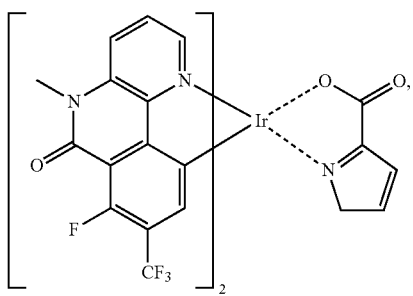
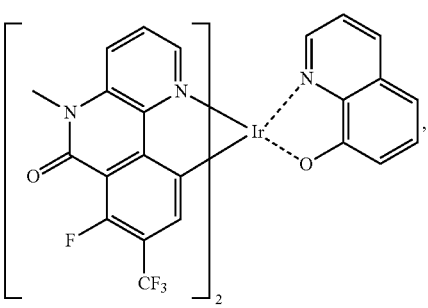
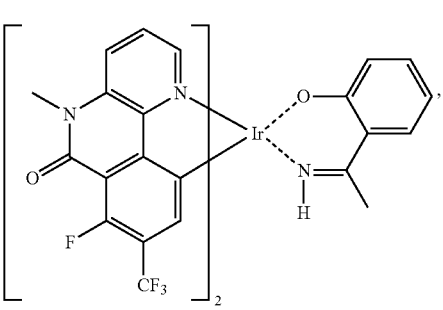
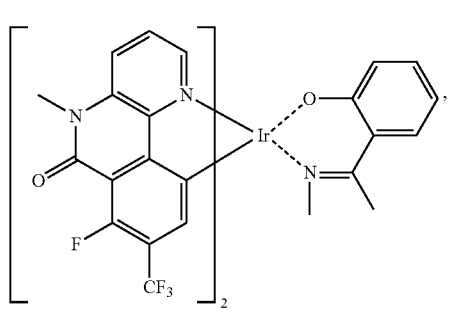
-continued
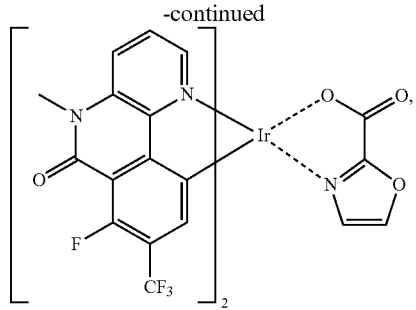
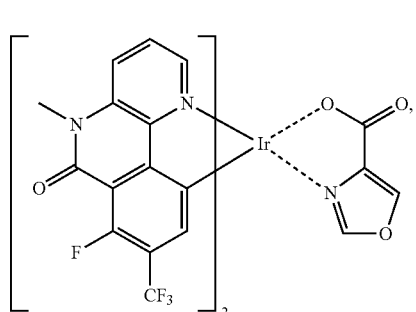
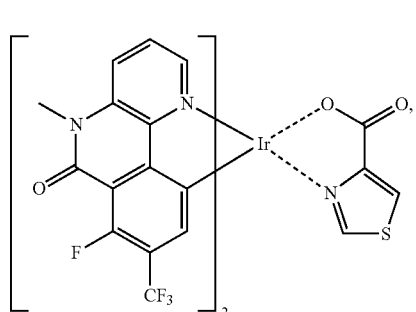
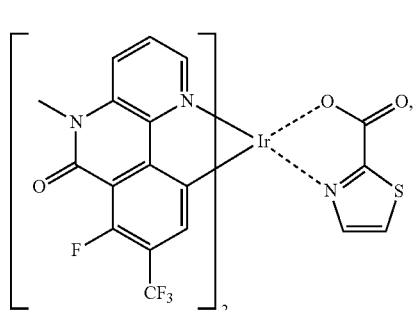
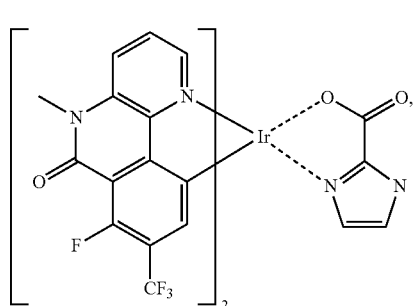

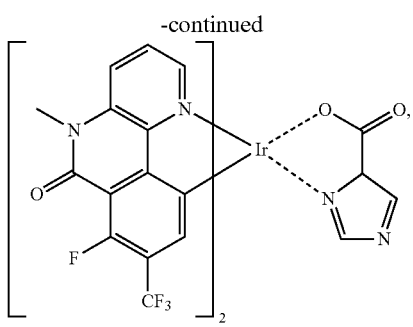
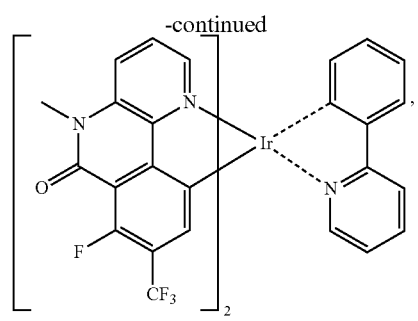
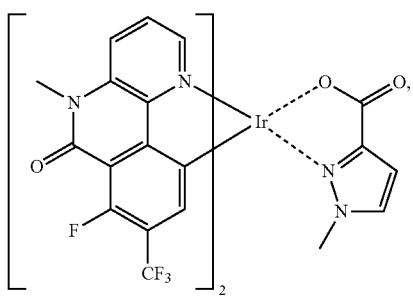
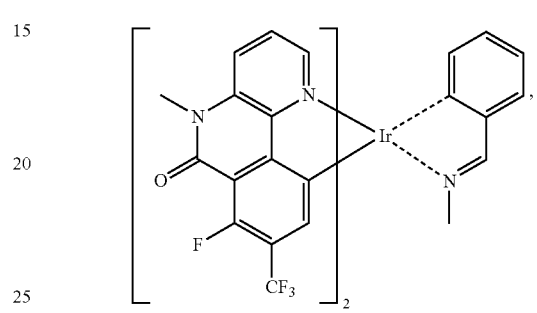
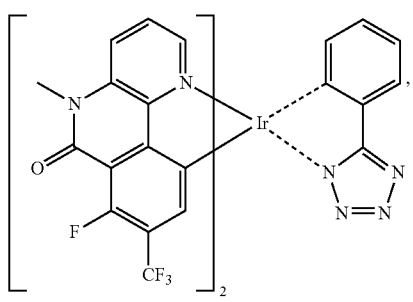
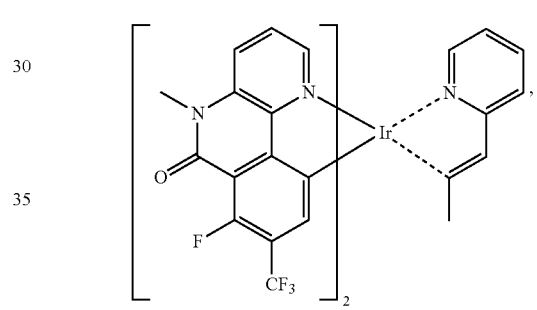
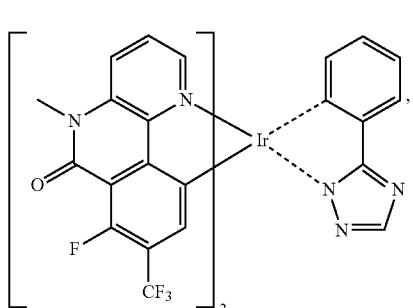
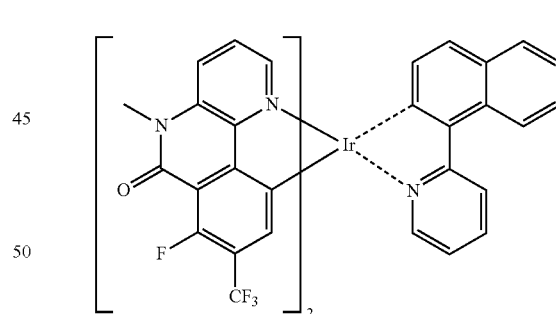
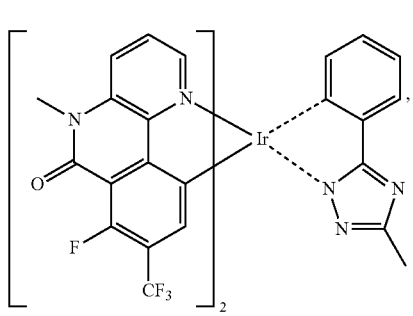
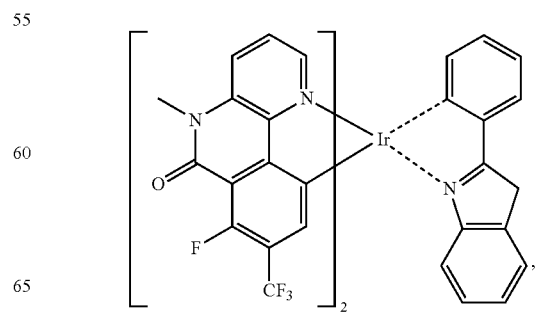

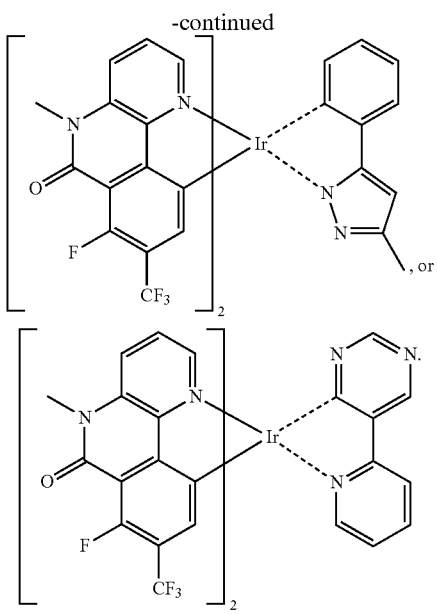

The following examples are intended to illustrate the disclosure more fully without limiting the scope, since numerous modifications and variations will be apparent to those skilled in this art.

Example 1: Preparation of Organic Metal Compound (I)

organic metal compound (I)

0.24 g (10.0 mmol) of sodium hydride (NaH) was added into a reaction bottle, and then the reaction bottle was vacuumized under a vacuum and refilled with nitrogen. 4 ml of tetrahydrofuran (THF) was added into the reaction bottle, and the mixture was stirred at 0° C. Next, 0.7 g (4.9 mmol) of compound (1) and 4 ml of tetrahydrofuran (THF) were added into the reaction bottle. After reacting for 30 min, 1.66 g (7.3 mmol) of compound (2) was added into the reaction bottle. After reacting at room temperature for 8 hr, the compound (1) was consumed completely (determined by nuclear magnetic resonance (NMR) or thin-layer chromatography (TLC)), and water was added into the reaction bottle to quench the reaction. Next, the result was extracted by ethyl acetate (EA) and an organic phase was collected. After removing the solvent, 1.14 g of compound (3) (solid) was obtained with a yield of 70%. The synthesis pathway of the above reaction was as follows:

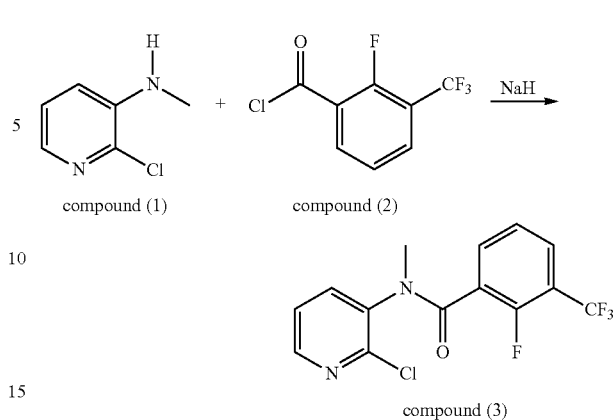

compound (1)   compound (2)

compound (3)

The physical measurement of the compound (3) is listed below: $^1$HnmR (400 MHz, CDCl$_3$): δ 8.2~98.27 (m, 1H), δ 7.7~7.71 (m, 1H), δ 7.6~7.64 (m, 1H), δ 7.53~7.49 (m, 1H), δ 7.2~7.22 (m, 1H), δ 7.1~7.15 (m, 1H), 3.43 (s, 3H).

2 g (6.0 mmol) of compound (3), 0.7 g (0.59 mmol) of Pd(PPh$_3$)$_4$, 3.18 g (30 mmol) of Na$_2$CO$_3$, and 30 ml of 2-(dimethylamino)ethyl methacrylate (DMA) were added into a reaction bottle. After heating at 150° C. for 4 hr, the compound (3) was consumed completely (determined by nuclear magnetic resonance (NMR) or thin-layer chromatography (TLC)), and water was added into the reaction bottle to quench the reaction. Next, the result was extracted three times by ethyl acetate (EA) and HCl (1M), and then an organic phase was collected. After removing the solvent, 1.3 g of compound (4) (solid) was obtained with a yield of 73%. The synthesis pathway of the above reaction was as follows:

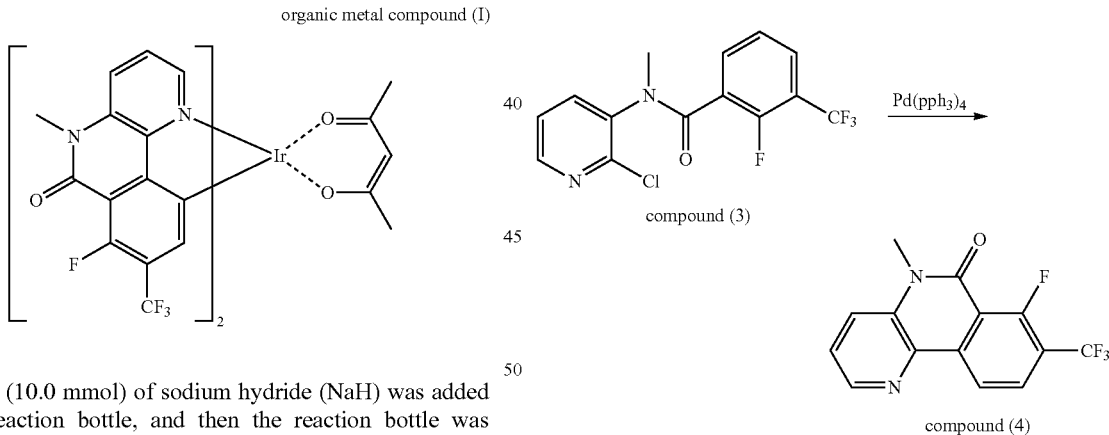

compound (3)

compound (4)

The physical measurement of the compound (4) is listed below: $^1$HnmR (400 MHz, CDCl$_3$): δ 8.82 (d, J=8.4 Hz, 1H), 8.63 (s, 1H), δ 8.01 (t, J=7.5 Hz, 1H), δ 7.72 (d, J=8.5 Hz, 1H), δ 7.5~87.57 (s, 1H), 3.76 (s, 3H). 102 mg (0.34 mmol) of compound (4), and 50 mg (0.17 mmol) of IrCl$_3$.H$_2$O were added into a reaction bottle. Next, 3 ml of 2-ethoxyethanol and 1 ml of water were added into the reaction bottle, and then the reaction bottle was heated at 120° C. with stirring. After reacting for 8 hr, the reaction bottle was cooled to room temperature, and then a solid was deposited. Next, the solvent was removed by rotary evaporation, and the result was washed by methanol. After removing the methanol, 102 mg of compound (5) (solid) was obtained with a yield of 74%. The synthesis pathway of the above reaction was as follows:

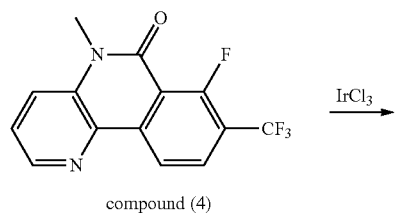

compound (4)

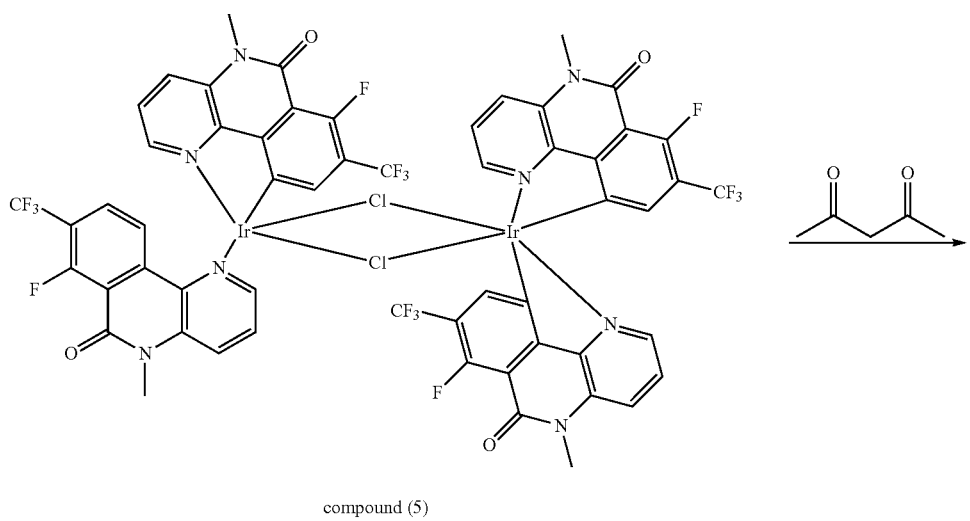

compound (5)

-continued

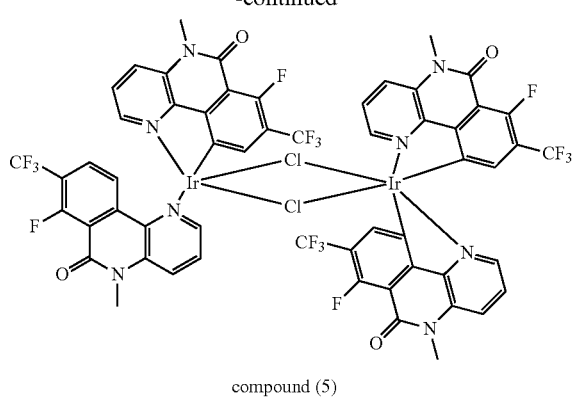

compound (5)

The physical measurement of the compound (5) is listed below: 1HnmR (400 MHz, CD2Cl2): δ 8.90 (d, J=5.7 Hz, 4H), δ 7.89 (d, J=8.7 Hz, 4H), δ 7.34 (s, 4H), 6.24 (s, 4H), 3.88 (s, 12H).

Next, 40 mg (0.024 mmol) of compound (5), 26 mg (0.24 mmol) of $Na_2CO_3$, 9.7 mg (0.098 mmol) of acetyl acetone, and 3 ml of 2-ethoxyethanol were added into a reaction bottle. Next, the reaction bottle was heated at 130° C. for 24 hr. After cooling to room temperature, the result was extracted three times by $CH_2Cl_2$ and water, and then an organic phase was collected. After drying over magnesium sulfate and rotary evaporation, the result was recrystallized by $CH_2Cl_2$/hexane, and then 30 mg of organic metal compound (I) (solid) was obtained with a yield of 70%. The synthesis pathway of the above reaction was as follows:

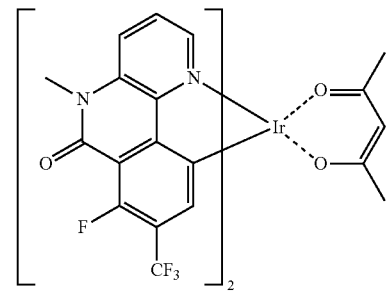

organic metal compound (I)

The physical measurement of the organic metal compound (I) is listed below: $^1$HnmR (400 MHz, $CDCl_3$): δ 8.37 (d, J=5.4 Hz, 2H), δ 7.74 (d, J=8.44 Hz, 2H), 8 7.59~7.56 (m, 2H), 8 6.59~6.53 (m, 2H), 3.81 (s, 6H), 1.84 (s, 6H).

Next, 0.29 mg of the organic metal compound (I) was dissolved in 5 ml of $CH_2Cl_2$, and the photoluminescence excitation spectrum of the organic metal compound (I) was measured, as shown in FIG. 1. The organic metal compound (I) had a maximum luminous intensity peak (Emission λmax) of 564 nm. Next, the quantum yield (ΦPL(%)) of the organic metal compound (I) was measured, and the result is shown in Table 1.

Example 2: Preparation of Organic Metal Compound (II)

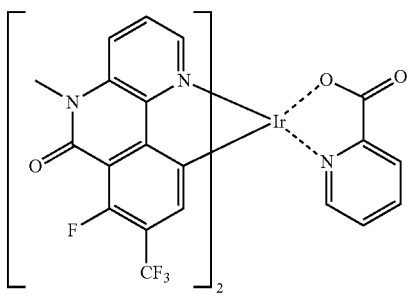

organic metal compound (II)

50 mg (0.03 mmol) of compound (5), 32 mg (0.3 mmol) of Na$_2$CO$_3$, 15 mg (0.12 mmol) of pyridine-2-carboxylic acid, and 3 ml of 2-ethoxyethanol were added into a reaction bottle. Next, the reaction bottle was heated at 130° C. for 24 hr. After cooling to room temperature, the result was extracted three times by CH$_2$Cl$_2$ and water, and then an organic phase was collected. After drying over magnesium sulfate and rotary evaporation, the result was recrystallized by CH$_2$Cl$_2$/hexane, and then 44 mg of organic metal compound (II) (solid) was obtained with a yield 80%. The synthesis pathway of the above reaction was as follows:

The physical measurement of the organic metal compound (II) is listed below: $^1$HnmR (400 MHz, CDCl$_3$): δ 8.72 (d, J=5.5 Hz, 1H), δ 8.39 (d, J=7.2 Hz, 1H), δ 8.02 (d, J=7.8 Hz, 1H), δ 7.77~7.74 (m, 3H), δ 7.61~7.58 (m, 1H), δ 7.50~7.39 (m, 1H), δ 7.38~7.37 (m, 2H), δ 6.77 (d, J=5.8 Hz, 1H), δ 8.53 (d, J=5.8 Hz, 1H), 3.81 (s, 6H).

Next, 0.31 mg of the organic metal compound (II) was dissolved in 5 ml of CH$_2$Cl$_2$, and the photoluminescence excitation spectrum of the organic metal compound (I) was measured, as shown in FIG. 1. The organic metal compound (II) had a maximum luminous intensity peak (Emission λmax) of 552 nm. Next, the quantum yield (φPL(%)) of the organic metal compound (II) was measured, and the result is shown in Table 1.

Comparative Example 1: Organic Metal Compound (III)

An organic metal compound (III) (having a structure of

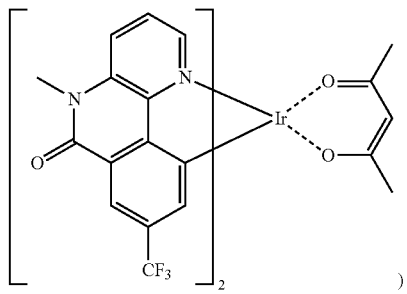

)

was provided (preparation of the organic metal compound (III) described in US20080214818A1). 0.26 mg of the

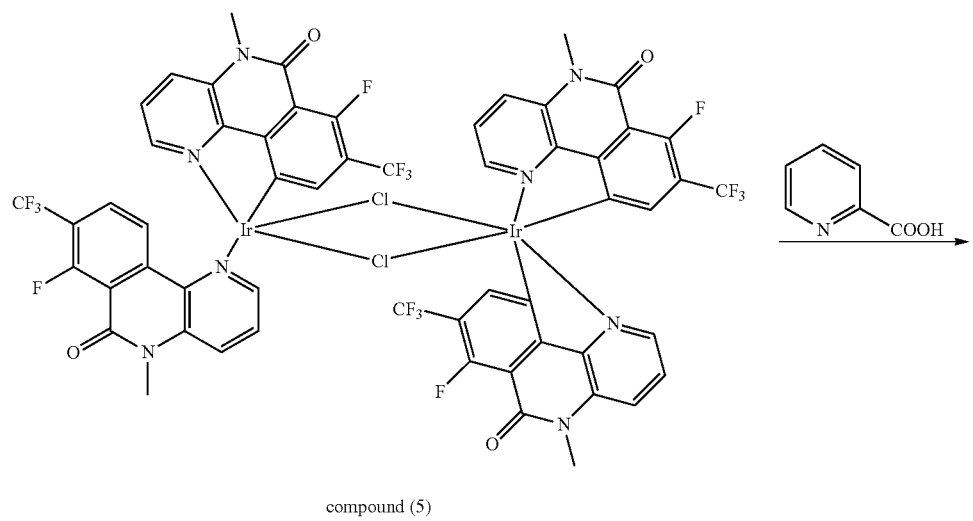

compound (5)

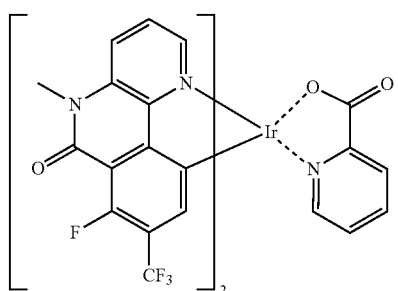

organic metal compound (II)

organic metal compound (III9) was dissolved in 5 ml of CH₂Cl₂, and the photoluminescence excitation spectrum of the organic metal compound (I) was measured, as shown in FIG. 1. The organic metal compound (III) had a maximum luminous intensity peak (Emission λmax) of 518 nm. Next, the quantum yield (φPL(%)) of the organic metal compound (III) was measured, and the result is shown in Table 1.

Comparative Example 2: Organic Metal Compound (IV)

An organic metal compound (IV) (having a structure of

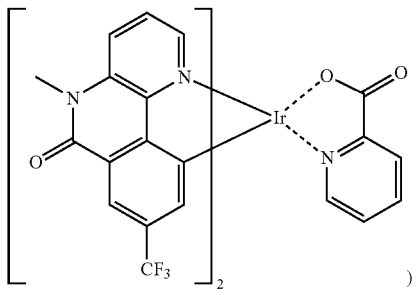

)

was provided (preparation of the organic metal compound (IV) described in US20080214818A1). 0.26 mg of the organic metal compound (III9) was dissolved in 5 ml of CH₂Cl₂, and the photoluminescence excitation spectrum of the organic metal compound (I) was measured, as shown in FIG. 1. The organic metal compound (IV) had a maximum luminous intensity peak (Emission λmax) of 513 nm. Next, the quantum yield (φPL(%)) of the organic metal compound (IV) was measured, and the result is shown in Table 1.

TABLE 1

| | maximum luminous intensity peak (Emission λmax) | quantum yield (ΦPL (%)) |
|---|---|---|
| organic metal compound (I) | 564 nm | 41 |
| organic metal compound (II) | 552 nm | 88 |
| organic metal compound (III) | 518 nm | 35 |
| organic metal compound (IV) | 513 nm | 72 |

As shown in FIG. 1, the maximum luminous intensity peak (564 nm, yellow) of the organic metal compound (I) (which has a structure of

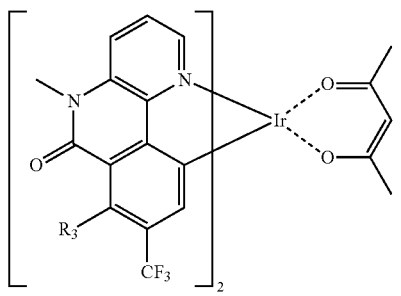

and R₃ is fluorine) can have a 46 nm red-shift in comparison with the maximum luminous intensity peak (518 nm, green) of the organic metal compound (III) (which has a structure of

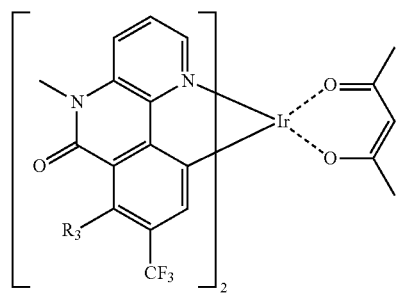

and R₃ is hydrogen); and the maximum luminous intensity peak (552 nm, yellow) of the organic metal compound (II) (which has a structure of

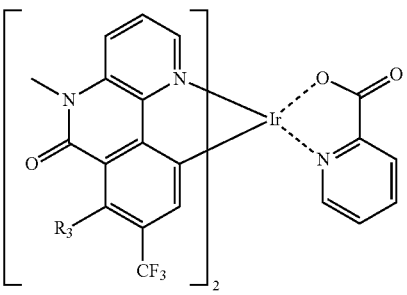

and R₃ is fluorine) can have a 39 nm red-shift in comparison with the maximum luminous intensity peak (513 nm, green) of the organic metal compound (IV) (which has a structure of

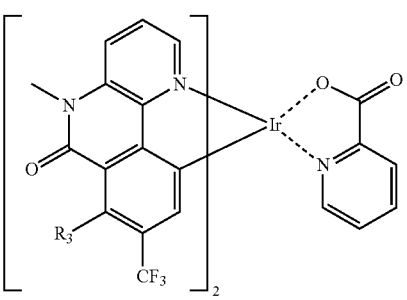

and R₃ is hydrogen).

Further, as shown in Table 1, the organic metal compound (I) has a quantum yield of 41%, which is about 1.22 times that of the organic metal compound (III) which has the same structure

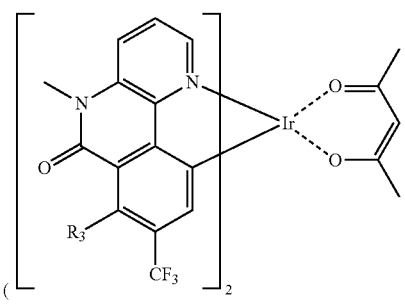

as the organic metal compound (I) except that R₃ is hydrogen rather than fluorine; and the organic metal compound (II) has a quantum yield of 88%, which is about 1.17 times that of the organic metal compound (IV) which has the same structure

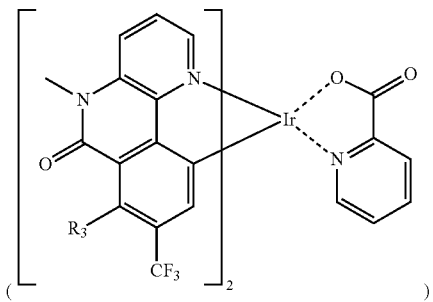

as the organic metal compound (II) except that $R_3$ is hydrogen rather than fluorine.

Organic Light-Emitting Device

Figure 2:
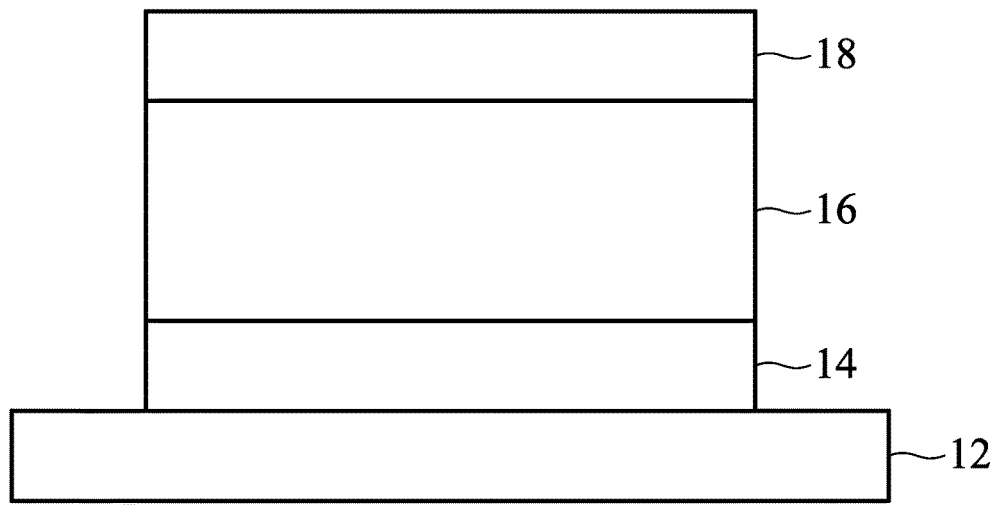
FIG. 2 shows a cross section of an organic light-emitting device disclosed by an embodiment of the disclosure.

FIG. 2 shows an embodiment of an organic light-emitting device 10. The organic light-emitting device 10 includes a substrate 12, a bottom electrode 14, an organic light-emitting element 16, and a top electrode 18, as shown in FIG. 2. The organic light-emitting device can be top-emission, bottom-emission, or dual-emission devices. The substrate 12 can be a glass, plastic, or semiconductor substrate. Suitable materials for the bottom and top electrodes can be Ca, Ag, Mg, Al, Li, In, Au, Ni, W, Pt, Cu, indium tin oxide (ITO), indium zinc oxide (IZO), aluminum zinc oxide (AZO), or zinc oxide (ZnO), formed by sputtering, electron beam evaporation, thermal evaporation, or chemical vapor deposition. Furthermore, at least one of the bottom and top electrodes 14 and 18 is transparent.

The organic light-emitting element 16 at least includes a light-emitting layer, and can further include a hole injection layer, a hole transport layer, an electron transport layer, and an electron injection layer. In embodiments of the disclosure, at least one layer of the organic light-emitting element 16 includes the aforementioned organic metal compound having Formula (I).

According to other embodiments of the disclosure, the organic light-emitting device can be a phosphorescent organic light-emitting device, and the light-emitting layer of the organic light-emitting element can include a host material and a dopant, wherein the dopant can include the aforementioned organic metal compound. The dose of the dopant is not limited and can be optionally modified by a person of ordinary skill in the field.

Figure 3:
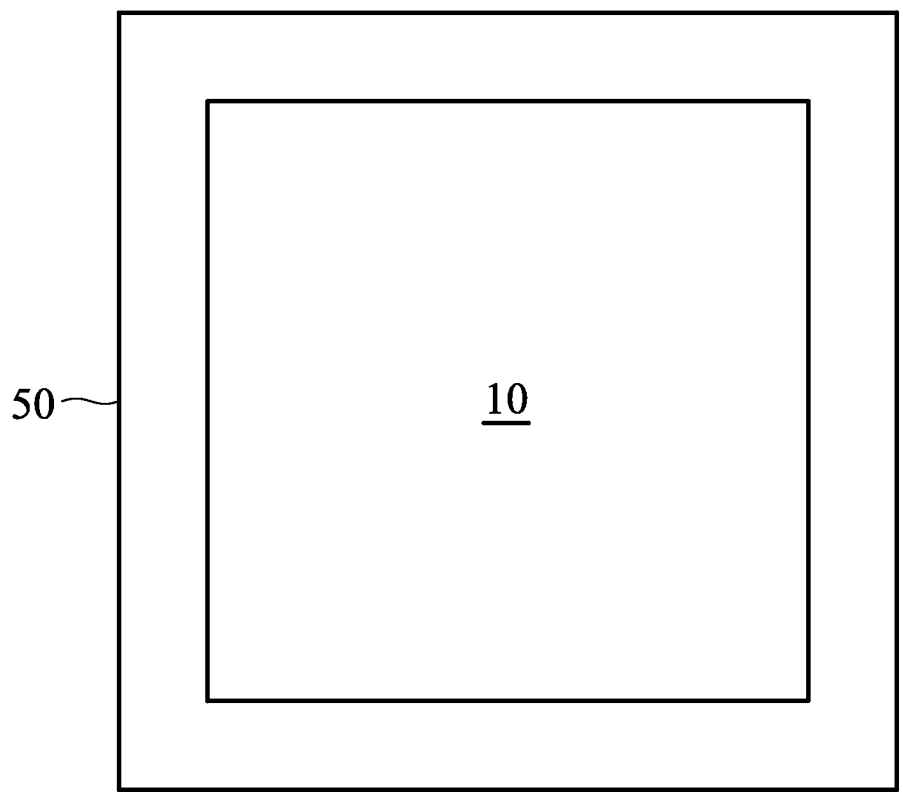
FIG. 3 schematically shows a block diagram of a lighting device according to an embodiment of the disclosure.

FIG. 3 schematically shows a block diagram of a lighting device 100 according to an embodiment of the disclosure. For example, the lighting device 100 can be an indoor light, a street lamp, a car light, or a back light source in a display device. The lighting device 100 of the disclosure can include the aforementioned organic light-emitting device 10 and a lead frame 50. In particular, the organic light-emitting device 10 is fixed on the lead frame 50, and the organic light-emitting device 10 connects to a power via the lead frame 50.

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:

1. An organic metal compound, having Formula (I):

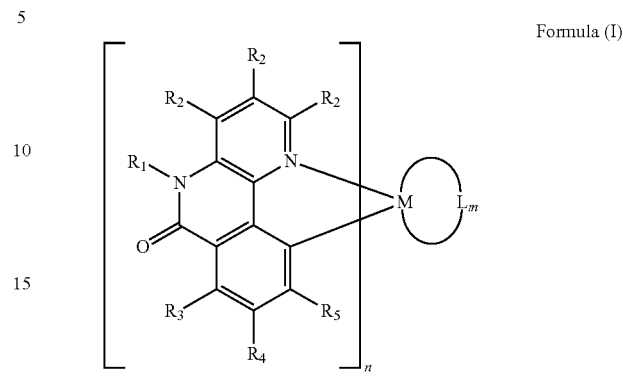

Formula (I)

wherein, M is Ir, Pt, Ru, Os, Cu, Au, or Pd; n is 1, 2, or 3, m is 0, 1, or 2, and a sum of m and n is equal to a valence of M; L is a bidentate ligand; $R_1$ is independently hydrogen, $C_{1-9}$ alkyl group, $C_{5-10}$ cycloalkyl group, or $C_{5-12}$ aromatic group; each of $R_2$ is independently hydrogen, halogen, cyano group, $C_{1-9}$ alkyl group, $C_{1-6}$ fluoroalkyl group, $C_{5-10}$ cycloalkyl group, or $C_{5-12}$ aromatic group; $R_3$ is halogen; $R_4$ and $R_5$ are independently hydrogen, hydroxyl group, amine group, alkyl amine group, halogen, cyano group, $C_{1-9}$ alkyl group, $C_{1-6}$ fluoroalkyl group, $C_{5-10}$ cycloalkyl group, or $C_{5-12}$ aromatic group; and, $R_3$, $R_4$, and $R_5$ are different.

2. The organic metal compound as claimed in claim 1, wherein $R_1$ is independently methyl group, ethyl group, propyl group, isopropyl group, butyl group, iso-butyl group, tert-butyl group, pentyl group, hexyl group, cyclohexyl group, phenyl group, biphenyl group, or naphthyl group.

3. The organic metal compound as claimed in claim 1, wherein $R_2$ is independently hydrogen, fluorine, chlorine, cyano group, methyl group, ethyl group, propyl group, isopropyl group, butyl group, iso-butyl group, tert-butyl group, pentyl group, hexyl group, fluoromethyl, fluoroethyl, cyclohexyl group, phenyl group, biphenyl group, or naphthyl group.

4. The organic metal compound as claimed in claim 1, wherein at least one of $R_2$ is not hydrogen.

5. The organic metal compound as claimed in claim 1, wherein $R_3$ is fluorine, or chlorine.

6. The organic metal compound as claimed in claim 1, wherein $R_4$ and $R_5$ are independently hydrogen, hydroxyl group, fluorine, chlorine, cyano group, amine group, dimethyl amine group, diethyl amine group, methyl group, ethyl group, propyl group, isopropyl group, butyl group, iso-butyl group, tert-butyl group, pentyl group, hexyl group, fluoromethyl, fluoroethyl, cyclohexyl group, phenyl group, biphenyl group, or naphthyl group.

7. The organic metal compound as claimed in claim 1, wherein L is bonded with M via an oxygen atom on one side, and bonded with M via another oxygen atom on the other side.

8. The organic metal compound as claimed in claim 7, wherein L is

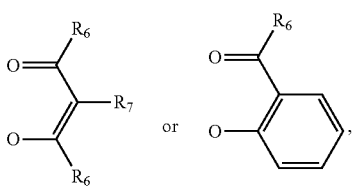

wherein each of $R_6$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group, and $R_7$ is hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group.

9. The organic metal compound as claimed in claim 1, wherein L is bonded with M via a nitrogen atom on one side, and bonded with M via another nitrogen atom on the other side.

10. The organic metal compound as claimed in claim 9, wherein L is

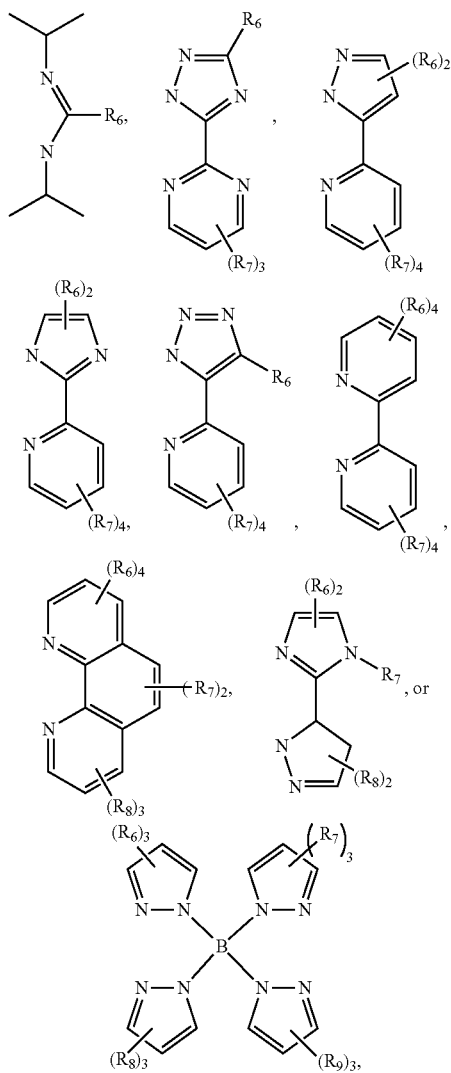

wherein each of $R_6$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; each of $R_7$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; each of $R_8$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; and, each of $R_9$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group.

11. The organic metal compound as claimed in claim 1, wherein L is bonded with M via a nitrogen atom on one side, and bonded with M via an oxygen atom on the other side.

12. The organic metal compound as claimed in claim 11, wherein L is

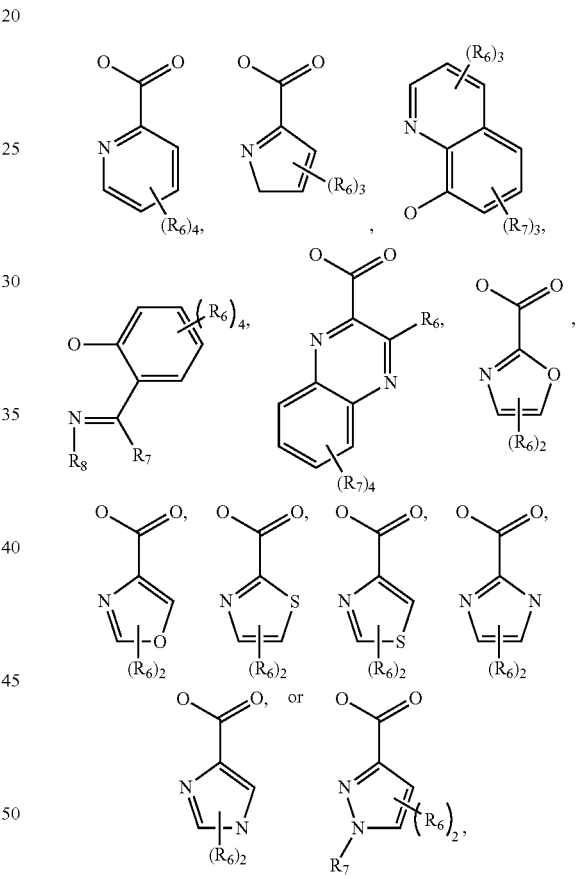

wherein each of $R_6$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; and, each of $R_7$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group.

13. The organic metal compound as claimed in claim 1, wherein L is bonded with M via a nitrogen atom on one side, and bonded with M via a carbon atom on the other side.

14. The organic metal compound as claimed in claim 13, wherein L is

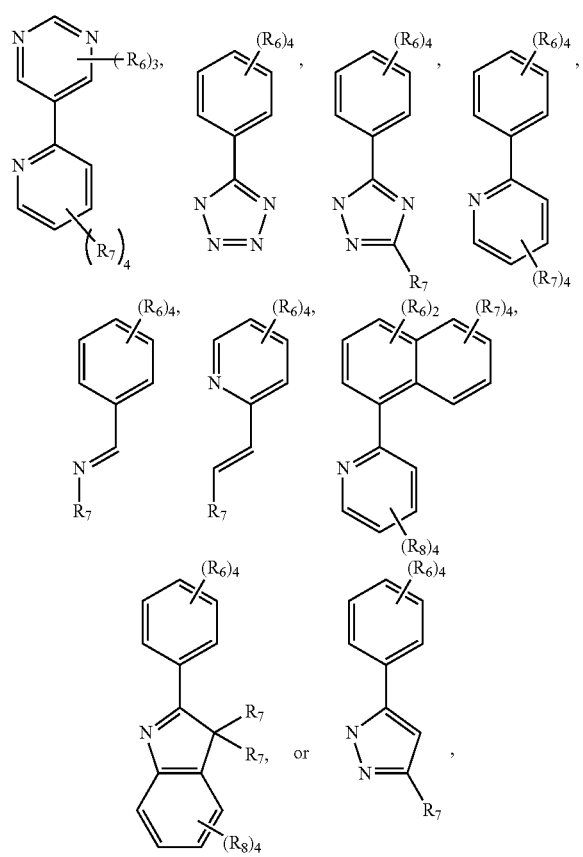

wherein each of $R_6$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; each of $R_7$ is independently hydrogen, halogen, $C_{1-9}$ alkyl group, C alkoxy group, $C_{1-6}$ fluoroalkyl group, $C_{5-10}$ cycloalkyl group, $C_{5-12}$ aromatic group, or $C_{2-8}$ heteroaryl group; and, each of $R_8$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group.

15. The organic metal compound as claimed in claim 1, wherein the organic metal compound is

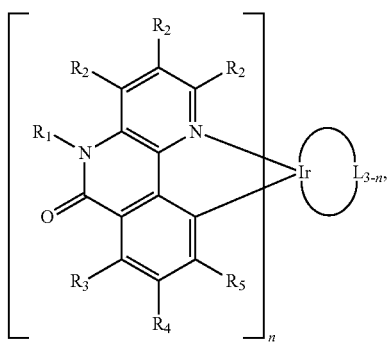

wherein n is 1, or 2; L is a bidentate ligand; $R_1$ is hydrogen, $C_{1-9}$ alkyl group, $C_{5-10}$ cycloalkyl group, or $C_{5-12}$ aromatic group; each of $R_2$ is independently hydrogen, halogen, cyano group, $C_{1-9}$ alkyl group, $C_{1-6}$ fluoroalkyl group, $C_{5-10}$ cycloalkyl group, or $C_{5-12}$ aromatic group; $R_3$ is halogen; and, $R_4$ and $R_5$ are independently hydrogen, hydroxyl group, amine group, alkyl amine group, halogen, cyano group, $C_{1-9}$ alkyl group, $C_{1-6}$ fluoroalkyl group, $C_{5-10}$ cycloalkyl group, or $C_{5-12}$ aromatic group.

16. The organic metal compound as claimed in claim 1, wherein the organic metal compound is

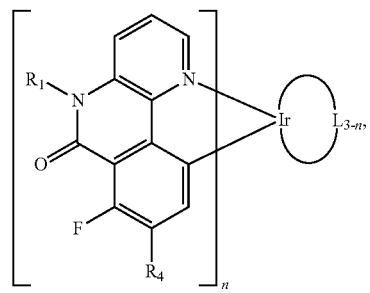

wherein n is 1, or 2; L is a bidentate ligand; $R_1$ is hydrogen, $C_{1-9}$ alkyl group, $C_{5-10}$ cycloalkyl group, or $C_{5-12}$ aromatic group; and, $R_4$ is hydrogen, hydroxyl group, amine group, alkyl amine group, halogen, cyano group, $C_{1-9}$ alkyl group, $C_{1-6}$ fluoroalkyl group, $C_{5-10}$ cycloalkyl group, or $C_{5-12}$ aromatic group.

17. The organic metal compound as claimed in claim 1, wherein the organic metal compound is

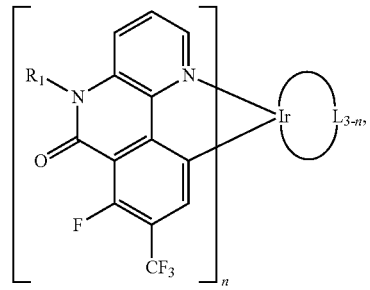

wherein n is 1, or 2; L is a bidentate ligand; and $R_1$ is hydrogen, $C_{1-9}$ alkyl group, $C_{5-10}$ cycloalkyl group, or $C_{5-12}$ aromatic group.

18. The organic metal compound as claimed in claim 1, wherein the organic metal compound is

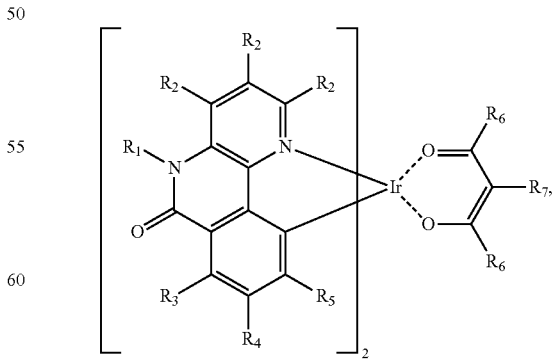

wherein $R_1$ is independently hydrogen, $C_{1-9}$ alkyl group, $C_{1-10}$ cycloalkyl group, or $C_{5-12}$ aromatic group; each of $R_2$ is independently hydrogen, halogen, cyano group, $C_{1-9}$ alkyl group, $C_{1-6}$ fluoroalkyl group, $C_{5-10}$ cycloalkyl group, or $C_{5-12}$ aromatic group; $R_3$ is halogen; $R_4$ and $R_5$ are independently hydrogen, hydroxyl group, amine group, alkyl amine group, halogen, cyano group, $C_{1-9}$ alkyl group, $C_{1-6}$ fluoroalkyl group, $C_{5-10}$ cycloalkyl group, or $C_{5-12}$ aromatic group; $R_6$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group; and, $R_7$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group.

19. The organic metal compound as claimed in claim 1, wherein the organic metal compound is

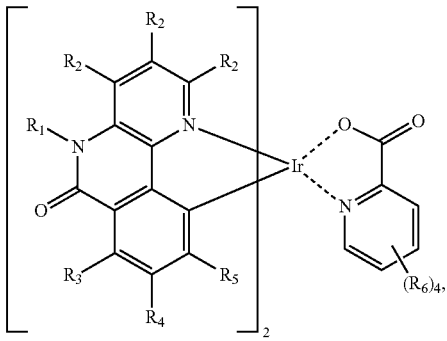

wherein $R_1$ is independently hydrogen, $C_{1-9}$ alkyl group, $C_{5-10}$ cycloalkyl group, or $C_{5-12}$ aromatic group; each of $R_2$ is independently hydrogen, halogen, cyano group, $C_{1-9}$ alkyl group, $C_{1-6}$ fluoroalkyl group, $C_{5-10}$ cycloalkyl group, or $C_{5-12}$ aromatic group; $R_3$ is halogen; $R_4$ and $R_5$ are independently hydrogen, hydroxyl group, amine group, alkyl amine group, halogen, cyano group, $C_{1-9}$ alkyl group, $C_{1-6}$ fluoroalkyl group, $C_{5-10}$ cycloalkyl group, or $C_{5-12}$ aromatic group; and, each of $R_6$ is independently hydrogen, halogen, $C_{1-9}$ alkyl group, $C_{1-9}$ alkoxy group, $C_{1-6}$ fluoroalkyl group, $C_{5-10}$ cycloalkyl group, $C_{5-12}$ aromatic group, or $C_{2-8}$ heteroaryl group.

20. An organic light-emitting device, comprising:
    a pair of electrodes; and
    an organic light-emitting element, disposed between the electrodes, wherein the organic light-emitting element comprises the organic metal compound as claimed in claim 1.

21. A lighting device, comprising:
    a lead frame; and
    the organic light-emitting device as claimed in claim 20, disposed on the lead frame.

* * * * *